United States Patent
McConnell et al.

(10) Patent No.: US 10,219,787 B2
(45) Date of Patent: Mar. 5, 2019

(54) RESPIRATORY MODE ("R-MODE")—ACQUISITION AND DISPLAY OF CARDIOVASCULAR IMAGES TO SHOW RESPIRATORY EFFECTS

(75) Inventors: Michael V. McConnell, Los Altos Hills, CA (US); Holden H. Wu, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 606 days.

(21) Appl. No.: 13/239,210

(22) Filed: Sep. 21, 2011

(65) Prior Publication Data

US 2012/0078083 A1    Mar. 29, 2012

Related U.S. Application Data

(60) Provisional application No. 61/387,631, filed on Sep. 29, 2010.

(51) Int. Cl.
*A61B 5/00*     (2006.01)
*A61B 8/08*     (2006.01)
(Continued)

(52) U.S. Cl.
CPC ............ *A61B 8/5284* (2013.01); *A61B 5/055* (2013.01); *A61B 6/037* (2013.01); *A61B 6/503* (2013.01);
(Continued)

(58) Field of Classification Search
CPC ....... A61B 5/055; A61B 8/5284; A61B 6/503; A61B 6/037; A61B 6/5288; A61B 8/0883; A61B 6/56
(Continued)

(56) References Cited

U.S. PATENT DOCUMENTS 4,716,368 A * 12/1987 Haacke .................. 324/309
5,320,093 A *  6/1994 Raemer ................ 128/203.12
(Continued)

OTHER PUBLICATIONS

Y Yang, S Rendig, S Siegel, D F Newport and SR Cherry, "Cardiac PET imaging in mice with simultaneous cardiac and respiratory gating", 2005, Physics in Medicine and Biology, vol. 50, pp. 2979-2989.*

(Continued)

*Primary Examiner* — Joel Lamprecht
(74) *Attorney, Agent, or Firm* — Beyer Law Group LLP (57) ABSTRACT

A computer implemented method for providing cardiovascular images over a respiratory cycle through a computer system is provided. A plurality of cardiovascular images is obtained. A cardiac phase is measured for each cardiovascular image of the plurality of cardiovascular images to associate each cardiovascular image to a cardiac phase. A respiratory phase is measured for each cardiovascular image of the plurality of cardiovascular images to associate each cardiovascular image to a respiratory phase. A first group of cardiovascular images with an associated first cardiac phase of the plurality of cardiovascular images is sorted in order of respiratory phases. The first group of cardiovascular images with the associated first cardiac phase of the plurality of cardiovascular images is displayed in order of respiratory phases.

13 Claims, 6 Drawing Sheets

(51) Int. Cl.
*A61B 5/055* (2006.01)
*A61B 6/03* (2006.01)
*A61B 6/00* (2006.01)

(52) U.S. Cl.
CPC .............. *A61B 6/5288* (2013.01); *A61B 6/56* (2013.01); *A61B 8/0883* (2013.01)

(58) Field of Classification Search
USPC ........................................................ 600/443
See application file for complete search history.

(56) References Cited

U.S. PATENT DOCUMENTS

| | | | | |
|---|---|---|---|---|
| 5,764,723 | A * | 6/1998 | Weinberger et al. | 378/65 |
| 6,198,959 | B1 * | 3/2001 | Wang | 600/413 |
| 6,704,593 | B2 * | 3/2004 | Stainsby et al. | 600/413 |
| 8,417,007 | B2 * | 4/2013 | Yui | 382/131 |
| 2004/0186372 | A1 * | 9/2004 | Boernert et al. | 600/410 |
| 2006/0100503 | A1 * | 5/2006 | Takai et al. | 600/422 |
| 2006/0170714 | A1 * | 8/2006 | Kanda | 346/2 |
| 2006/0224062 | A1 * | 10/2006 | Aggarwal et al. | 600/413 |
| 2007/0055142 | A1 * | 3/2007 | Webler | 600/425 |
| 2007/0073142 | A1 * | 3/2007 | Eck | A61B 6/481 600/413 |
| 2007/0101295 | A1 * | 5/2007 | Ding et al. | 715/838 |
| 2007/0106149 | A1 * | 5/2007 | Mistretta | A61B 5/055 600/410 |
| 2008/0221439 | A1 * | 9/2008 | Iddan et al. | 600/424 |
| 2009/0130641 | A1 * | 5/2009 | Mahesh et al. | 434/262 |
| 2009/0220050 | A1 * | 9/2009 | Guhring | A61B 5/055 378/98.5 |
| 2010/0280358 | A1 * | 11/2010 | Mata | A61B 5/0813 600/420 |

OTHER PUBLICATIONS

McConnell, Michael V. "Respiratory-Mode Display of Echocardiographic Images Highlights Effects of Pericardial Disease" JACC: Cardiovascular Imaging, vol. 6, No. 8., Dec. 12, 2013.

* cited by examiner

RESPIRATORY MODE ("R-MODE")—ACQUISITION AND DISPLAY OF CARDIOVASCULAR IMAGES TO SHOW RESPIRATORY EFFECTS

CROSS REFERENCE TO RELATED APPLICATIONS

This application claims priority under 35 U.S.C. § 119 from U.S. Provisional Patent Application No. 61/387,631, filed Sep. 29, 2010, entitled RESPIRATORY MODE ("R-MODE")—ACQUISITION AND DISPLAY OF CARDIOVASCULAR IMAGES TO SHOW RESPIRATORY EFFECTS which is incorporated herein by reference for all purposes.

BACKGROUND OF THE INVENTION

This invention relates generally to cardiovascular imaging.

Cardiovascular imaging may use various imaging processes such as echocardiography or cardiovascular magnetic resonance imaging (MRI) to image the cardiovascular system.

SUMMARY OF THE INVENTION

In accordance with the invention, a computer implemented method for providing cardiovascular images over a respiratory cycle through a computer system is provided. A plurality of cardiovascular images is obtained. A cardiac phase is measured for each cardiovascular image of the plurality of cardiovascular images to associate each cardiovascular image to a cardiac phase. A respiratory phase is measured for each cardiovascular image of the plurality of cardiovascular images to associate each cardiovascular image to a respiratory phase. A first group of cardiovascular images with an associated first cardiac phase of the plurality of cardiovascular images is sorted in order of respiratory phases. The first group of cardiovascular images with the associated first cardiac phase of the plurality of cardiovascular images is displayed in order of respiratory phases.

In another manifestation of the invention, an apparatus for providing cardiovascular images over a respiratory cycle is provided. A system for receiving the cardiovascular image data for a plurality of cardiovascular images comprises at least one processor and computer readable media. The computer readable media comprises computer readable code for associating each cardiovascular image of the plurality of cardiovascular images with a cardiac phase, computer readable code for associating each cardiovascular image of the plurality of cardiovascular images with a respiratory phase, computer readable code for sorting a first group of cardiovascular images with an associated first cardiac phase of the plurality of cardiovascular images in order of respiratory phase, and computer readable code for creating a video display of images for at least one cardiac phase in order of respiratory phase.

The invention and objects and features thereof will be more readily apparent from the following detailed description and appended claims when taken with the drawings.

BRIEF DESCRIPTION OF THE DRAWINGS

FIGS. 5 A-D show images from a 54 year old male.

DETAILED DESCRIPTION OF ILLUSTRATED EMBODIMENTS

Several cardiac conditions, such as pericardial constriction and tamponade, and diastolic dysfunction, cause variation in chamber sizes with respiration, as can be seen by echocardiography. As these changes can be intermittent and subtle, and with motion dominated by cardiac contraction, the respiratory effects can be missed, particularly by less experienced sonographers or physicians-in-training. Recognition is important in order to guide additional and longer acquisitions that further evaluate respiratory effects. Traditionally, images are acquired and displayed to show cardiac motion over the cardiac cycle and then respiratory changes must be visualized in the setting of cardiac contraction. Also, it is now common for echo laboratories to acquire loops of only one or two heartbeats at a time, to limit data storage demands, so these respiratory effects may not even occur during the acquisition.

Figure 1:
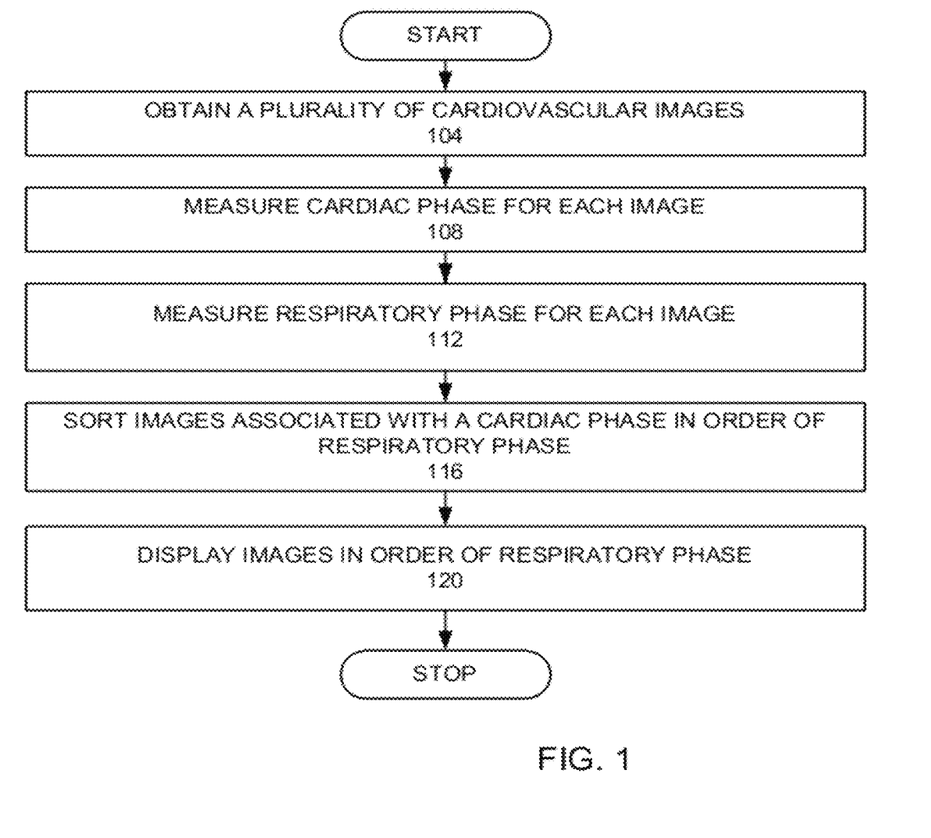
FIG. 1 is a high level flow chart of an embodiment of the invention.

To facilitate understanding of the invention, FIG. 1 is a high level flow chart of an embodiment of the invention. A plurality of cardiovascular images are obtained (step 104). A cardiac phase is measured for each cardiovascular image so that each cardiovascular image is associated with a cardiac phase (step 108). A respiratory phase is measured for each cardiovascular image so that each cardiovascular image is associated with a respiratory phase (step 112). The images are sorted for a cardiac phase in order of respiratory phase (step 116). The images for the cardiac phase are displayed in order of respiratory phase (step 120).

An embodiment of the invention acquires and/or displays cardiovascular images, such that only changes over the respiratory cycle are displayed with cardiac motion kept fixed. This can be done by 1) acquiring images during respiration and also acquiring cardiac cycle and respiratory cycle information with the image data, 2) sorting the image data by their phase in the respiratory and cardiac cycles, and 3) displaying images over the respiratory cycle, keeping the cardiac phase fixed.

An implementation of this method would be an additional acquisition/display option on an echo or MRI scanner (e.g., Respiratory Mode or "R-Mode") such that when the user selects this option, the image data are acquired and displayed to show only respiratory effects. Effectively this would be a software program to acquire/display the image data in a novel way.

In a general example, when images are acquired during respiration, each will have an associated cardiac phase (C1, C2, C3, . . . CN) derived from a cardiac signal (e.g., electrocardiogram (ECG), pulse-oxygenation plethysmograph (PG), self navigator, or navigator measurement) and an associated respiratory phase (R1, R2, R3, . . . RM) derived from a respiratory signal (e.g., impedance, pneumatic bellows, self navigator, or navigator measurement). The image data is then sorted so images can be displayed in a cine (video) format to cover the respiratory cycle (R1-RM) while keeping the cardiac phase fixed. The displayed movies (R-Mode) would then show only the dynamic effects of respiration for each (fixed) phase of the cardiac cycle (C1:R1-RM, C2:R1-RM, C3:R1-RM, . . . CN:R1-RM).

The main application is in cardiovascular imaging, as a novel enhancement to current capabilities to improve the visualization of respiratory changes on the heart. The most common respiratory changes that can occur with disease are shifts in the position of the interventricular septum with inspiration as well as changes in the size/shape of the right ventricle. The most common diseases where these findings can aid in the diagnosis are constrictive pericarditis, pericardial tamponade, and pulmonary embolism.

Example 1

In an example of an embodiment of the invention, a continuous cardiovascular MRI acquisition during breathing is used to obtain a plurality of cardiovascular MRI images (step 104) over one or more respiratory cycles. In this example, a 2D spiral k-space trajectory was used for MRI spatial encoding. The full set of spiral readouts was divided into several subsets (segments) and each segment (of acquisition duration $T_{Seg}$) was collected multiple times to fully sample the cardiac and respiratory cycles before moving on to the next segment.

Figure 2:
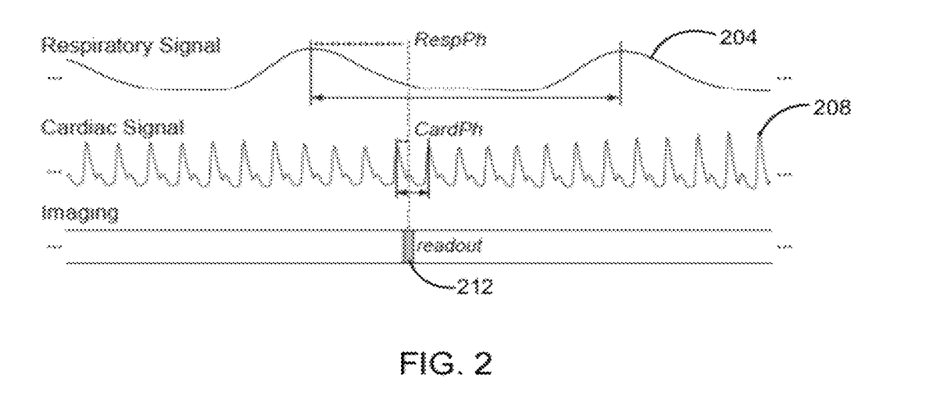
FIG. 2 is a graph showing a measured respiratory signal and a measured cardiac signal.

Cardiac and respiratory information were concurrently recorded during the scan from monitoring devices. In this example, a PG signal was used to measure cardiac phase (step 108), and pneumatic bellows were used to measure respiratory phase (step 112). FIG. 2 is a graph showing a measured respiratory signal 204 and a measured cardiac signal 208.

The acquired MRI data was then retrospectively synchronized to the cardiac and respiratory motion. Based on the recorded physiologic signals, the respiratory and cardiac phases of each readout were retrospectively determined from the readout's relative temporal position within the local respiratory and cardiac cycles to associate the data with cardiac phase and respiratory phase. The slope of the pneumatic bellows signal was used to identify the onset of inspiration. The number of respiratory and cardiac phases to reconstruct were quantized to ($T_{RespAvg}/T_{CardAvg}$) and ($T_{CardAvg}/T_{Seg}$), respectively, where $T_{RespAvg}$ is the average respiratory cycle duration, $T_{CardAvg}$ is the average cardiac cycle duration, and $T_{Seg}$ is the duration of one acquisition segment. FIG. 2 illustrates how readout data for an MRI image 212 is associated with cardiac phase and respiratory phase.

Figure 3:
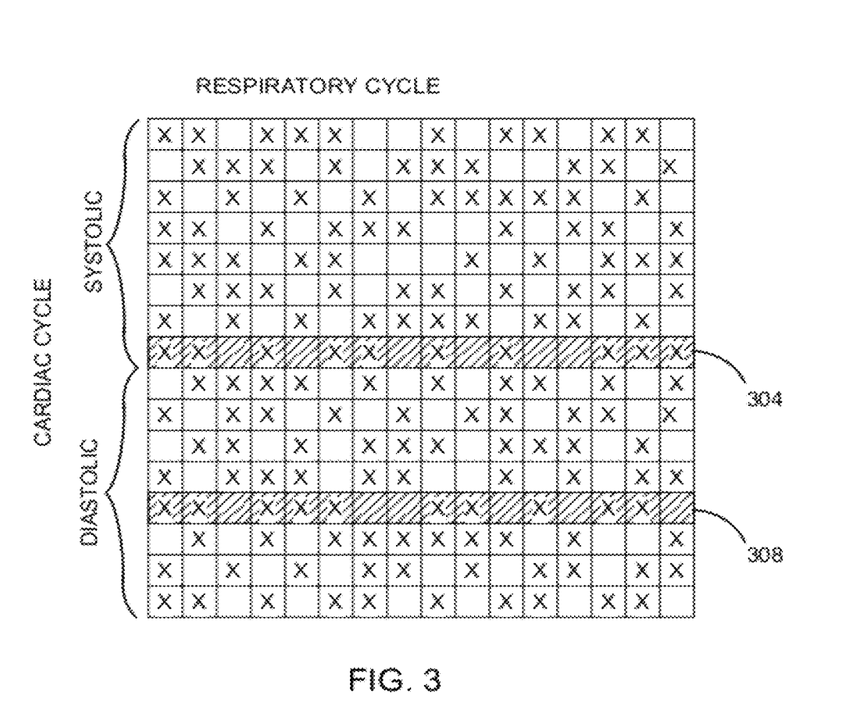
FIG. 3 is a schematic illustration of a matrix of cardiac phase and respiratory phase. Each position in the matrix represents a cardiovascular image at the corresponding cardiac and respiratory phase.

To reconstruct an image for each desired phase of cardiac and respiratory motion, data is sorted/organized into a multi-dimensional matrix of dimensions [2D spatial information, 1D cardiac motion, 1D respiratory motion]. Since the cardiac and respiratory cycles are not synchronized in general, there may be missing/incomplete data points or repeated acquisitions of the same data point in this matrix. In this example, missing/incomplete data are filled in from neighboring points using interpolation and repeated instances of the same data point are averaged. FIG. 3 is a simplified 2D representation of the multi-dimensional data matrix where each location corresponds to a 2D cardiovascular image at a specific cardiac phase and respiratory phase. The diastolic and systolic parts of the cardiac phase are labeled. The "X" marks indicate the cardiac phase and respiratory phase locations in the matrix where a complete 2D MRI image is acquired at least once. Other positions not marked by an "X" may have either none or only part of the desired cardiovascular image and are filled in from neighboring "X" locations. 2D cardiovascular images are then reconstructed for each desired respiratory and cardiac phase combination (temporal resolution is $T_{Seg}$ for each cardiac phase and $T_{CardAvg}$ for each respiratory phase). In this example, an end-systolic cardiac phase 304 and mid-diastolic cardiac phase 308 (indicated by shading) are selected for reconstruction and display.

Figure 4:
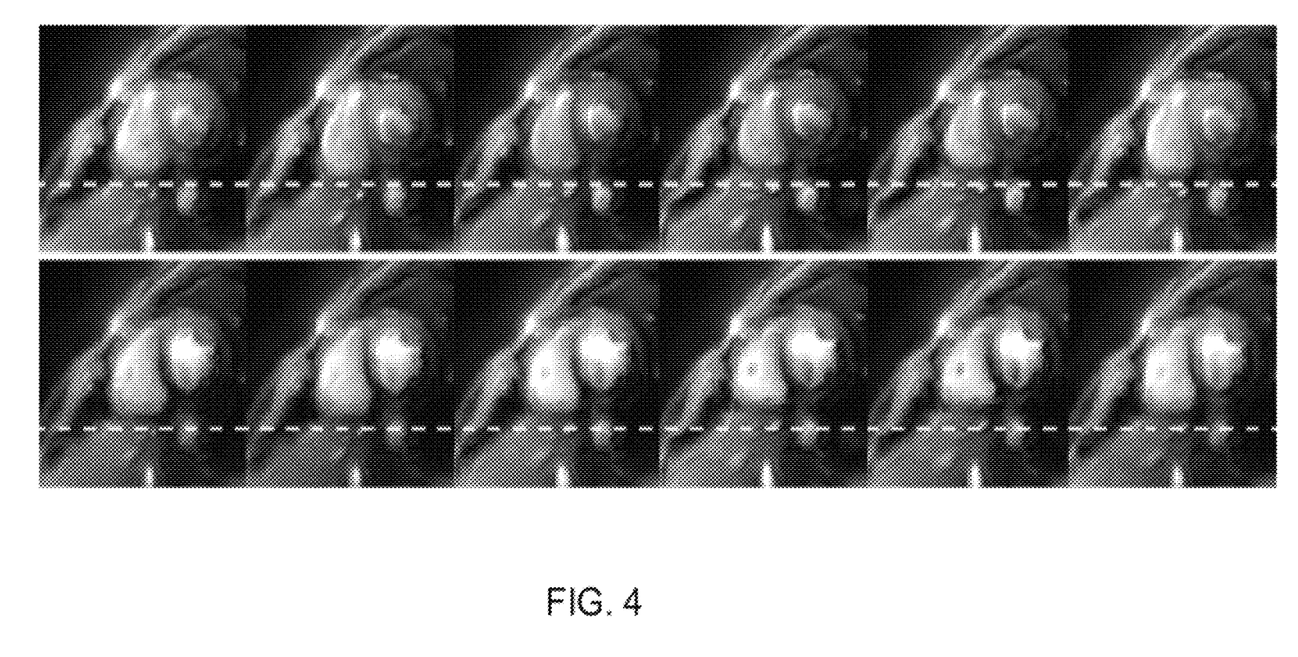
FIG. 4 shows a plurality of MRI images, where the top row of MRI images are from an end-systolic cardiac phase and the bottom row are from a mid-diastolic cardiac phase where the MRI images in each row are in order of respiratory phase.

2D cardiovascular images are displayed as a temporal sequence with respect to respiratory motion at each stage of the cardiac cycle, i.e. R-mode MRI as shown in FIG. 4 (step 120). FIG. 4 shows a plurality of MRI images, where the top row of MRI images are from an end-systolic cardiac phase and the bottom row are from a mid-diastolic cardiac phase and where the MRI images in each row are in order of respiratory phase.

Example 2

In another example, a prospectively gated MRI acquisition of the heart and/or blood vessels is performed during breathing over one or more respiratory cycles. The data matrix is first initialized with blank entries that occupy the desired dimensions [2D spatial information, 1D cardiac motion, 1D respiratory motion]. Cardiac and respiratory information are continuously monitored during the scan from standard monitoring devices (ECG, PG, bellows) and/or MRI navigator signals, and the cardiac and respiratory phase information are continually determined and associated with the present moment in time (steps 108 and 112) while the image data is obtained (step 104).

Prospective synchronization of acquired MRI data to monitored cardiac and respiratory motion is used to acquire and reconstruct a plurality of MRI images. If a desired cardiac and respiratory phase location in the data matrix is encountered during the scan from prospective gating, a controller enables the MRI system for data acquisition to update the data matrix. This approach effectively associates and sorts/organizes acquired image data into the matrix (step 116). In this process, one or more cardiac or respiratory phases may not be obtained or stored at all. After concluding data acquisition, missing/incomplete entries are filled in from neighboring complete data points and repeated data points are averaged. 2D cardiovascular images are reconstructed for each desired cardiac and respiratory phase.

2D cardiovascular images are displayed as a temporal sequence with respect to respiratory motion at each stage of the cardiac cycle, i.e. R-mode MRI (step 120).

Variations:

In other embodiments, other k-space acquisition trajectories are used for MRI spatial encoding. Additional magnetization-preparation modules can be incorporated to enhance MRI contrast. Multiple receiver elements and other advanced constrained reconstruction techniques may be employed to reduce scan time and estimate incomplete/missing data (e.g., parallel imaging, compressed sensing, variable-density sampling, and modeling of signal behavior). In other embodiments, additional functional information, such as flow or perfusion, is acquired in the MRI procedure and the functional maps are reconstructed and displayed in R-mode. In other embodiments, multiple slices are acquired and displayed in R-mode. In other embodiments, other signals correlated to cardiac and respiratory motion are utilized for synchronization. In other embodiments, imaging contrast agents are administered. In other embodiments, the imaging region of interest extends beyond the heart, such as in the blood vessels. In other embodiments, the imaging subject is non-human. In other embodiments, the plurality of cardiovascular images may be a subset of a larger number of cardiovascular images.

This invention can apply to all imaging modalities, such as echocardiography, radio isotope imaging, positron emission tomography (PET), single photon emission computed tomography (SPECT), X-ray, computed tomography (CT) or cardiovascular MRI images. Cardiovascular MRI is another example, like echocardiography, where images are typically displayed over the cardiac cycle. MRI data acquired during respiration can be resorted to display over the respiratory cycle. There are several ways to acquire the respiratory signal. One is to use impedance information from the ECG to derive a respiratory signal. The other is to use a pneumatic bellows over the patient's chest. There are also several MRI approaches, including navigator imaging of the diaphragm position or so-called self-navigator signal derived from the MRI data. There are also many ways to consider processing the respiratory signal, including the level vs. slope of the respiratory signal/diaphragm position, or a combination.

A major advantage is that the images will display only the respiratory effects of the disease and remove the confounding dynamic changes due to cardiac contraction. For example, a normal heart displayed in this way will show minimal motion, without changes in cardiac chamber size/shape. With disease, in contrast, the change in chamber size/shape will be virtually the only change in the images. This is advantageous in two ways. One is that by removing the other dynamic information from the image display, it will be easier to detect the presence or absence of respiratory effects associated with disease. The second is that some respiratory effects are most evident when there is a coincidence of the right respiratory phase (e.g., inspiration) with the right cardiac phase (e.g., diastole). Displaying/observing continuous images, as is done currently, may not capture this coincidence reliably and the respiratory effects may be missed.

A novel feature is an additional acquisition/display option for cardiovascular imaging—"R-Mode." This will allow the user (i.e., imaging physician) to acquire/review these additional images focusing on displaying respiratory effects. This would be an added feature on echo or MRI machines and/or image workstations to perform additional acquisitions or process the acquisitions with this method and display them to the user.

An embodiment of the invention helps solve a clinical problem, which is detecting the presence or absence of respiratory changes in cardiac chambers or blood vessels that can lead to the correct clinical diagnosis.

Figure 5:
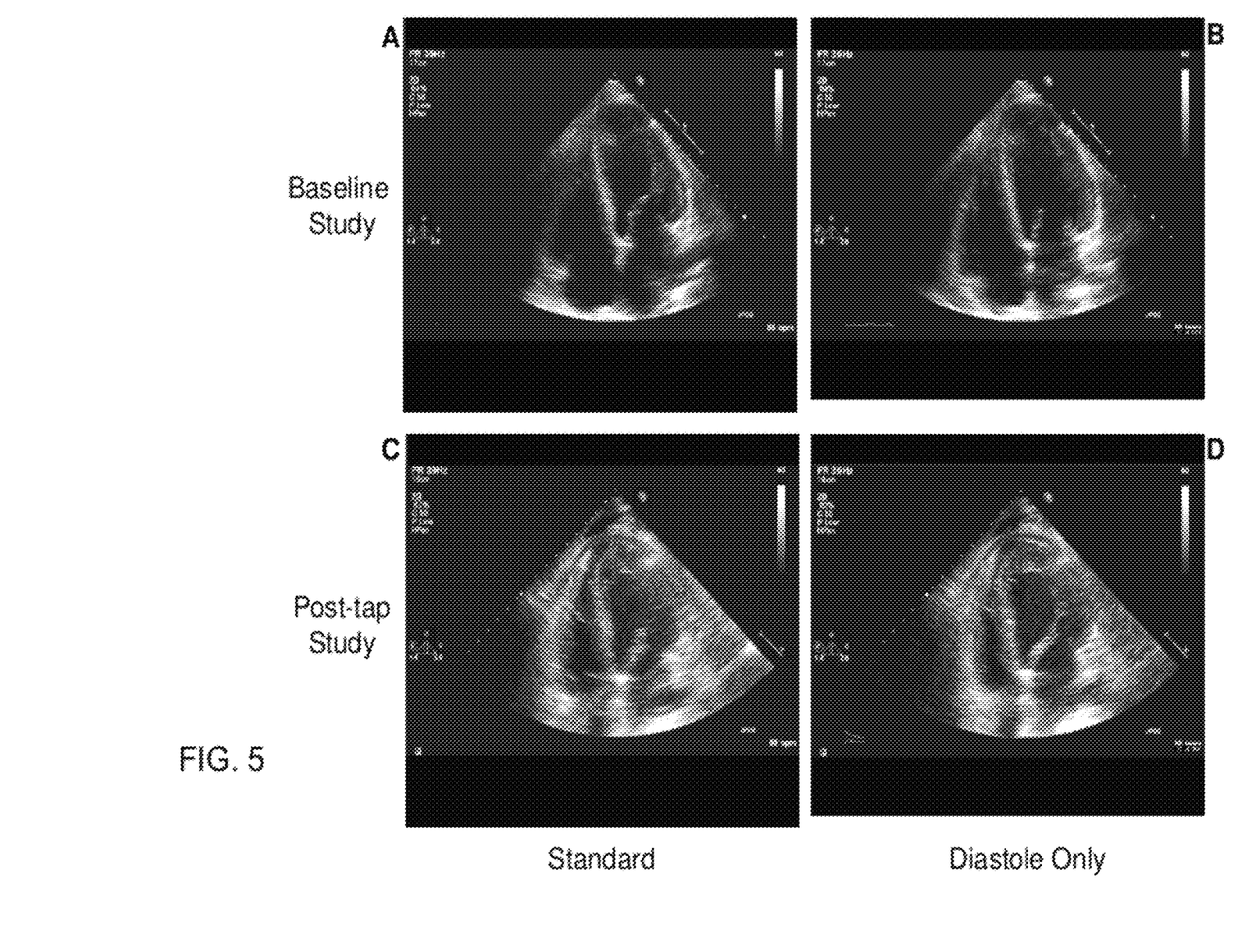

In another example, for a patient, a septal shift was noted intermittently on the standard 4-chamber echo acquisition. The septal shift became much more obvious as the main motion when only displaying the 10 end-diastolic images as a R-mode loop. In this example, the 54 year old male underwent echocardiography related to chemotherapy for Hodgkin's disease (FIGS. 5 A-D). The baseline echocardiogram showed normal LV systolic function without significant respiratory changes in the left ventricle (LV) or RV, as shown in FIG. 5A. Minimal cardiac motion and lack of respiratory changes are clearly shown when only diastolic images are displayed, as shown in FIG. 5B. Shortly after starting chemotherapy, the patient was diagnosed with Staph Aureus bacteremia and then developed a small pericardial effusion. This was found to be purulent on pericardiocentesis, with high LV and RV filling pressure persisting despite a drop in pericardial pressure. An echocardiogram at this time showed a thickened pericardium with intermittent leftward septal shift or "bounce," consistent with constrictive physiology, as shown in FIG. 5C. The "R-mode" display of diastolic images re-ordered based on respiratory phase nicely highlights the septal shift that occurs from expiration to inspiration, as shown in FIG. 5D.

Figure 6:
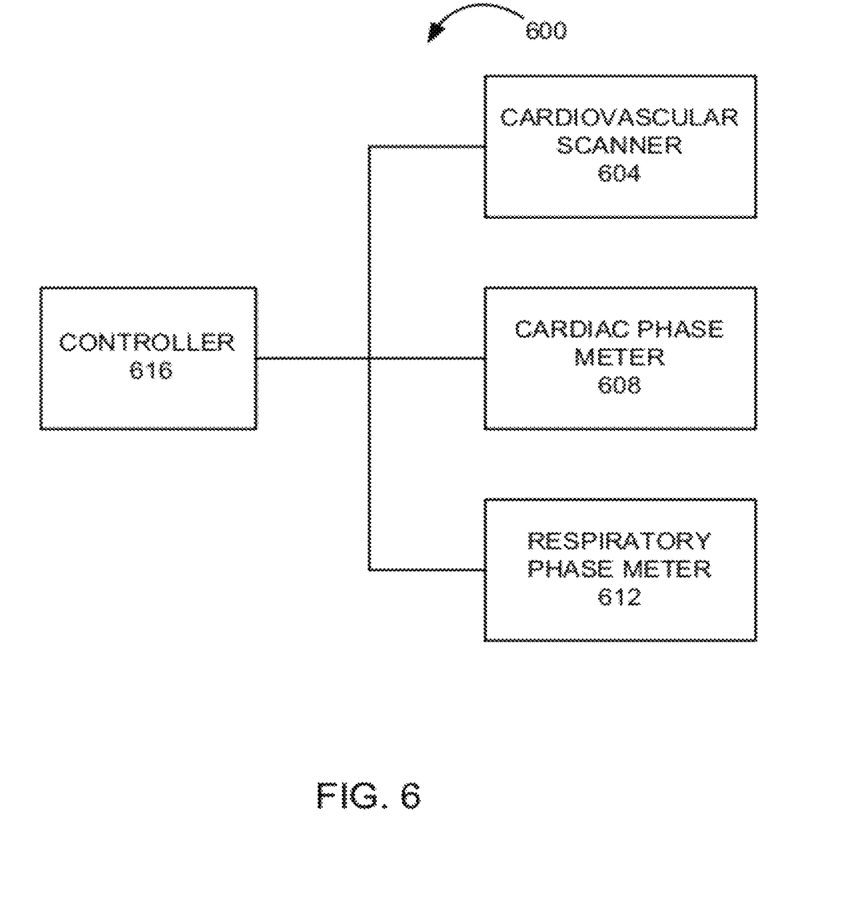
FIG. 6 is a block diagram of a system that may be used in an embodiment of the invention.

FIG. 6 is a block diagram of a system 600 that may be used in an embodiment of the invention. The system 600 comprises a cardiovascular scanner 604, a cardiac phase meter 608, a respiratory phase meter 612, and a controller 616 controllably connected to the cardiovascular scanner 604, the cardiac phase meter 608, and the respiratory phase meter 612. The cardiovascular scanner 604 may be an MRI system for imaging the cardiovascular system, an echocardiography system, a radio isotope imaging system, a positron emission tomography imaging system, a single photon emission computed tomography system, x-ray, or computed tomography system. The cardiac phase meter 608 may be an ECG system, a PG system, a self navigator system, or a navigator measurement system. The self navigator system would use images that are processed to generate the cardiac phase. The respiratory phase meter 612 may be bellows, an impedance system, self navigator system, pneumatic bellows, or navigator measurement system. Although the cardiovascular scanner 604, the cardiac phase meter 608, and the respiratory phase meter 612 are shown separately, in some embodiments two or three of these systems may be combined. For example, MRI navigator signals may be used to provide respiratory phase. This would then combine the cardiovascular scanner 604 and respiratory phase meter 612 into a single system.

Figure 7:
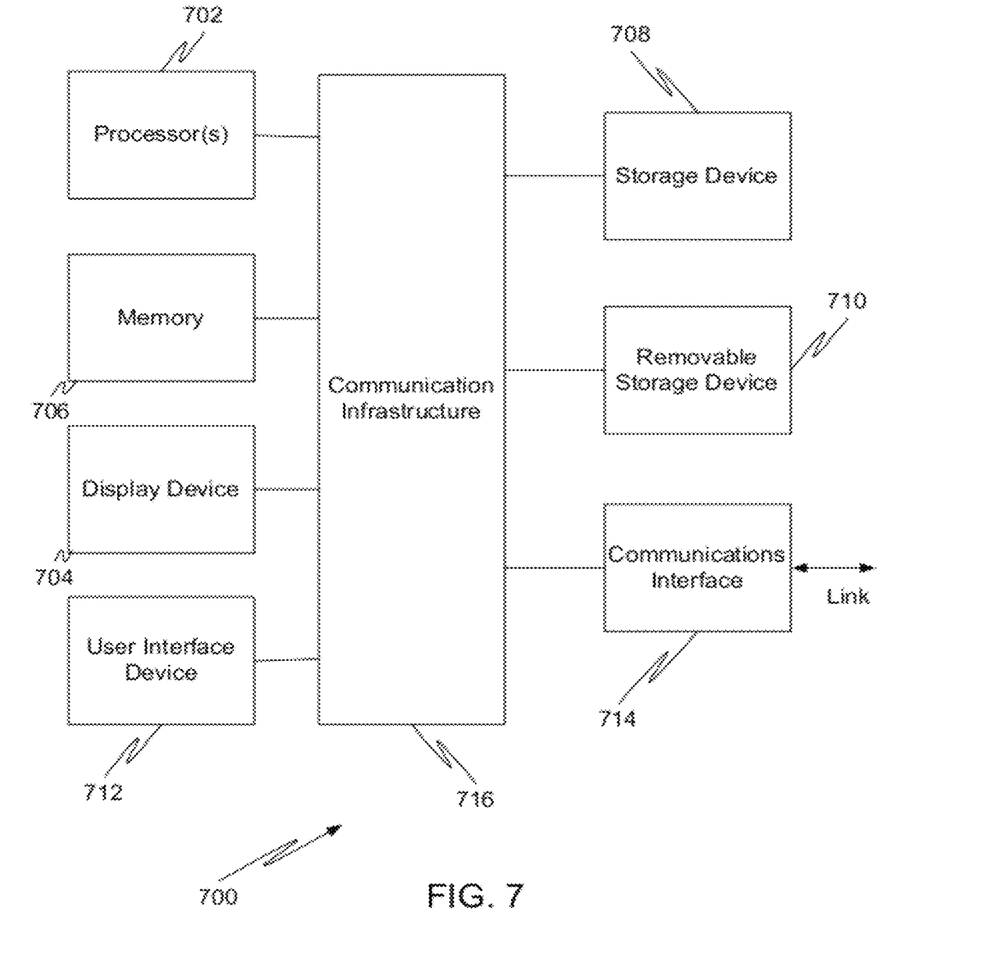
FIG. 7 is a high level block diagram showing a computer system, which is suitable for implementing a controller used in embodiments of the present invention.

FIG. 7 is a high level block diagram showing a computer system 700, which is suitable for implementing a controller 616 used in embodiments of the present invention. The computer system may have many physical forms ranging from an integrated circuit, a printed circuit board, and a small handheld device up to a huge super computer. The computer system 700 includes one or more processors 702, and further can include an electronic display device 704 (for displaying graphics, text, and other data), a main memory 706 (e.g., random access memory (RAM)), storage device 708 (e.g., hard disk drive), removable storage device 710 (e.g., optical disk drive), user interface devices 712 (e.g., keyboards, touch screens, keypads, mice or other pointing devices, etc.), and a communication interface 714 (e.g., wireless network interface). The communication interface 714 allows software and data to be transferred between the computer system 700 and external devices via a link. The system may also include a communications infrastructure 716 (e.g., a communications bus, cross-over bar, or network) to which the aforementioned devices/modules are connected.

Information transferred via communications interface 714 may be in the form of signals such as electronic, electromagnetic, optical, or other signals capable of being received by communications interface 714, via a communication link that carries signals and may be implemented using wire or cable, fiber optics, a phone line, a cellular phone link, a radio frequency link, and/or other communication channels. With such a communications interface, it is contemplated that the one or more processors 702 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Another embodiment of the invention may comprise a computer system for generating cardiovascular images over a respiratory cycle, comprising an input port for receiving a plurality cardiovascular images, a port for respiratory phase information, a port for receiving cardiac phase information, computer readable code for associating each cardiovascular image of the plurality of cardiovascular images with a cardiac phase, which is determined from the cardiac phase information, computer readable code for associating each cardiovascular image of the plurality of cardiovascular images with a respiratory phase, which is determined from the respiratory phase information, computer readable code for sorting a first group of cardiovascular images with an associated first cardiac phase of the plurality of cardiovascular images in order of respiratory phases, and computer readable code for creating a video display of images for at least one cardiac phase in order of respiratory phase. A video display may be any moving image display or format, such as a cine display. Such a system may be attached to an imaging system. Such systems may use a single port to receive the cardiovascular images, the respiratory phase information, and/or the cardiac phase information. In one embodiment, the information may be provided by a single port, since the same information may be used to provide images and/or cardiac phase and/or respiratory phase, as described above. In another variation, the images may be displayed on the imaging system or another device.

In another embodiment, the cardiovascular images may be images that indicate blood flow in either the heart or blood vessels. In echocardiograms, a Doppler shift may be used to measure blood flow. In MRI, different methods such as phase contrast and Fourier velocity encoding may be used to measure blood flow. Generally, flow changes significantly over the cardiac cycle. This embodiment of the invention allows the measurement of the change of flow over the respiratory cycle. This would also be useful in assessing diastolic dysfunction.

In some embodiments, images are obtained over a plurality of respiratory cycles. Collecting images over a plurality of respiratory cycles, allows images in one cycle to fill in gaps of another cycle. In other embodiments, images are obtained over only one cycle or less than one cycle. In CT processes this may be desirable to reduce radiation exposure time. Whether one or more respiratory cycles are measured, the display may display only one respiratory cycle or less than one respiratory cycle. This may be done by combining data from more than one cycle to one or less cycles.

Another embodiment would use the above described prospective approach with CT imaging. In such a process, CT x-ray exposure would be minimized or paused during one or more specified cardiac phases, so that data is not obtained during those cardiac phases. As a result, CT radiation exposure is reduced. Data from specified cardiac phases during CT x-ray exposure would be used to generate images.

Various embodiments may under sample the image data and then use a reconstruction to provide images. In a CT system, such a process allows the reduction of CT radiation exposure.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A computer implemented method for providing cardiovascular images over a respiratory cycle through a computer system, to display a respiratory effect of at least one of constrictive pericarditis, pericardial tamponade, or pulmonary embolism, comprising:
    obtaining a plurality of cardiovascular images using a cardiovascular scanner in chronological order over a plurality of respiratory cycles;
    measuring a cardiac phase for each cardiovascular image of the plurality of cardiovascular images to associate each cardiovascular image to a cardiac phase using a cardiac phase meter;
    measuring a respiratory phase for each cardiovascular image of the plurality of cardiovascular images to associate each cardiovascular image to a respiratory phase using a respiratory phase meter;
    creating on the computer system a video of changes of the heart at a first cardiac phase of the plurality of cardiovascular images in progressional order of respiratory phases, comprising the steps of:
        reordering the cardiovascular images of the first cardiac phase images from chronological order to respiratory cycle order, wherein if a first respiratory phase of the first cardiac phase an image is not obtained and wherein if a second respiratory phase of the first cardiac phase repeated acquisitions are obtained;
        interpolating neighboring images of respiratory phases of the first cardiac phase to generate an image for the first respiratory phase of the first cardiac phase; and
        replacing the repeated acquisitions obtained for the second respiratory phase of the first cardiac phase with a single image generated from the repeated acquisitions obtained for the second respiratory phase of the first cardiac phase; and
    displaying the video of changes on the heart at the first cardiac phase of the plurality of cardiovascular images in progressional order of respiratory phases.

2. The computer implemented method, as recited in claim 1, further comprising:
    creating on the computer system a video of changes of the heart at a second cardiac phase of the plurality of cardiovascular images in progressional order of respiratory phases, comprising the steps of:

reordering the cardiovascular images of the second cardiac phase images from chronological order to respiratory cycle order;

wherein if a third respiratory phase of the second cardiac phase an image is not obtained and wherein if a fourth respiratory phase of the second cardiac phase repeated acquisitions are obtained:

interpolating neighboring images of respiratory phases of the second cardiac phase to generate an image for the third respiratory phase of the second cardiac phase; and replacing the repeated acquisitions obtained for the fourth respiratory phase of the second cardiac phase with a single image generated from the repeated acquisitions obtained for the fourth respiratory phase of the second cardiac phase; and displaying the video of changes of the heart at the second cardiac phase of the plurality of cardiovascular images in progressional order of respiratory phases.

3. The computer implemented method, as recited in claim 2, wherein the plurality of cardiovascular images are echocardiography, radio isotope imaging, positron emission tomography, single photon emission computed tomography, x-ray, computed tomography or cardiovascular MRI images.

4. The computer implemented method, as recited in claim 3, wherein the respiratory phase meter comprises an at least one of an impedance meter, bellows, self navigator, or navigator meter.

5. The computer implemented method, as recited in claim 4, wherein the cardiac phase meter comprises an at least one of a pulse-oxygenation plethysmograph, electrocardiogram, self navigator or navigator meter.

6. The computer implemented method, as recited in claim 3, wherein the obtaining the plurality of cardiovascular images obtains and stores cardiovascular images from all cardiac phases.

7. The computer implemented method, as recited in claim 6, wherein the reordering the cardiovascular images, comprises placing the cardiovascular images in a matrix with dimensions of cardiac phase and respiratory phase.

8. The computer implemented method, as recited in claim 3, wherein the obtaining the plurality of cardiovascular images does not store or does not obtain and store cardiovascular images from at least one cardiac phase.

9. The computer implemented method, as recited in claim 1, wherein the obtaining the plurality of cardiovascular images does not obtain any cardiovascular images from at least one cardiac phase.

10. An apparatus for providing cardiovascular images over a respiratory cycle, to display a respiratory effect of at least one of constrictive pericarditis, pericardial tamponade, or pulmonary embolism, comprising:

a system for receiving the cardiovascular image data for a plurality of cardiovascular images, comprising:
at least one processor; and
computer readable media, comprising:
computer readable code for associating each cardiovascular image of the plurality of cardiovascular images with a cardiac phase;
computer readable code for associating each cardiovascular image of the plurality of cardiovascular images with a respiratory phase;
computer readable code for sorting a first group of cardiovascular images with an associated first cardiac phase of the plurality of cardiovascular images in order of respiratory phases; and
computer readable code for creating a video of images at a first cardiac phase in progressional order of respiratory phase, wherein the video display of images shows respiratory effects of at least one of constrictive pericarditis, pericardial tamponade, or pulmonary embolism, comprising the steps of:
reordering the cardiovascular images for the first cardiac phase images from chronological order to respiratory cycle order, wherein if a first respiratory phase of the first cardiac phase an image is not obtained and wherein if a second respiratory phase of the first cardiac phase repeated acquisitions are obtained;
interpolating neighboring images of respiratory phases of the first cardiac phase to generate an image for the first respiratory phase of the first cardiac phase; and
replacing the repeated acquisitions obtained for the second respiratory phase of the first cardiac phase with a single image generated from the repeated acquisitions obtained for the second respiratory phase of the first cardiac phase.

11. The apparatus, as recited in claim 10, further comprising:
a cardiovascular imager for obtaining a plurality of cardiovascular images electrically connected to the system for receiving the cardiovascular image data;
a respiratory phase meter for measuring respiratory phase electrically connected to the system for receiving the cardiovascular image data;
a cardiac phase meter for measuring cardiac phase electrically connected to the system for receiving the cardiovascular image data; and
a display electrically connected to the system for receiving the cardiovascular image data,
wherein the computer readable media further comprises computer readable code for displaying the video of images on the display.

12. The computer implemented method, as recited in claim 1, wherein the replacing the plurality of images obtained for the second respiratory phase of the first cardiac phase with a single image generated from the plurality of images obtained for the second respiratory phase of the first cardiac phase, comprises averaging together the plurality of images obtained for the second respiratory phase of the first cardiac phase.

13. A computer implemented method for providing cardiovascular images over a respiratory cycle through a computer system, to display a respiratory effect of at least one of constrictive pericarditis, pericardial tamponade, or pulmonary embolism, comprising:

obtaining a plurality of cardiovascular images using a cardiovascular scanner in chronological order;
measuring a cardiac phase for each cardiovascular image of the plurality of cardiovascular images to associate each cardiovascular image to a cardiac phase using a cardiac phase meter;
measuring a respiratory phase for each cardiovascular image of the plurality of cardiovascular images to associate each cardiovascular image to a respiratory phase using a respiratory phase meter;
creating on the computer system a re-ordered series of cardiovascular images corresponding to the first cardiac phase of the plurality of cardiovascular images in order of respiratory phases, comprising the steps of:

(1) selecting all the images from the plurality of cardiovascular images that correspond to the first cardiac phase; and
(2) re-ordering the selected images from step (1) in progressional order of respiratory phases; and displaying the re-ordered series of cardiovascular images as a video corresponding to the first cardiac phase in progressional order of respiratory phases, which shows changes in cardiovascular images with respect to respiratory motion to display a respiratory effect of at least one of constrictive pericarditis, pericardial tamponade, or pulmonary embolism.

\* \* \* \* \*